(12) United States Patent
Sarem et al.

(10) Patent No.: US 6,475,777 B1
(45) Date of Patent: Nov. 5, 2002

(54) CELL AND TISSUE CULTURE UNIT WITH VARIABLE CONFIGURATION

(75) Inventors: Farzin Sarem, Vandoeuvre-les-Nancy (FR); Leila-Ouassila Sarem Damerdji, Vandoeuvre-les-Nancy (FR)

(73) Assignee: Cell Tissue Progress, Paris (FR)

( * ) Notice: Subject to any disclaimer, the term of this patent is extended or adjusted under 35 U.S.C. 154(b) by 120 days.

(21) Appl. No.: 09/665,704

(22) Filed: Sep. 20, 2000

(30) Foreign Application Priority Data

Apr. 27, 2000 (FR) .......................................... 00 05413

(51) Int. Cl.⁷ ................................................ C12M 1/24
(52) U.S. Cl. ................. 435/304.1; 435/297.5; 435/305.3
(58) Field of Search ........................... 435/297.1, 297.2, 435/297.5, 304.1, 305.3

(56) References Cited

U.S. PATENT DOCUMENTS

| 5,190,878 A | 3/1993 | Wilhelm .................... 435/285 |
| 5,789,251 A | 8/1998 | Astle ........................... 436/48 |
| 5,817,510 A | 10/1998 | Pandey et al. ........... 435/305.3 |

FOREIGN PATENT DOCUMENTS

| DE | 298 15 276 | 7/1999 |
| EP | 0 307 048 | 3/1989 |
| WO | WO 98/27195 | 6/1998 |

*Primary Examiner*—David A. Redding
(74) *Attorney, Agent, or Firm*—Young & Thompson

(57) ABSTRACT

A cell and tissue culture unit comprises a base (1) equipped with access means (7,8) for being connected to a culture medium feed device and delimiting at least side-walls (5) of a culture chamber (6) and at least side-walls of at least a well (3-i) communicating through at least one of its upper and lower portions with chamber (6), as well as removable closing means (10,15-i,17i) able to provide access to chamber (6) and to well (3-i).

11 Claims, 3 Drawing Sheets

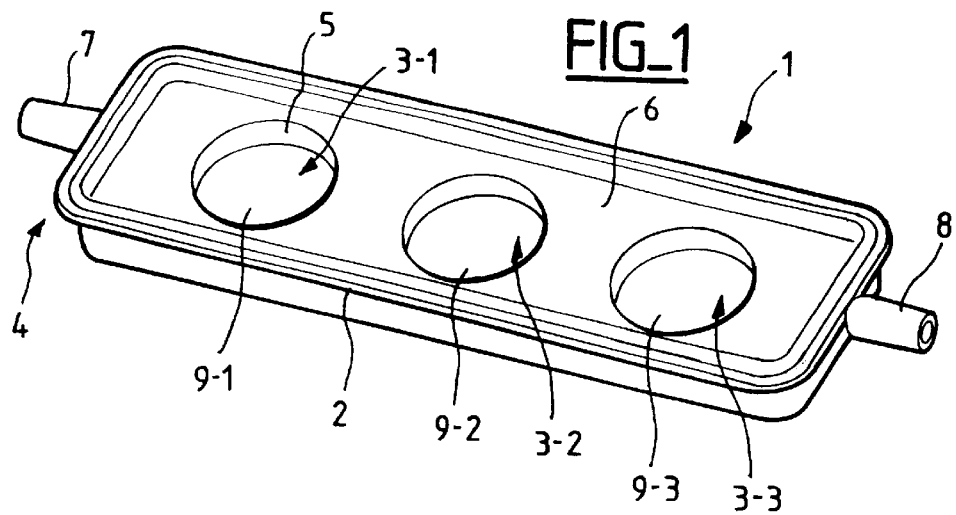
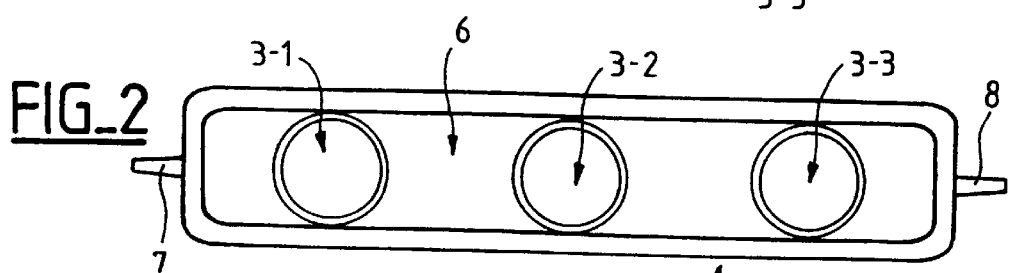
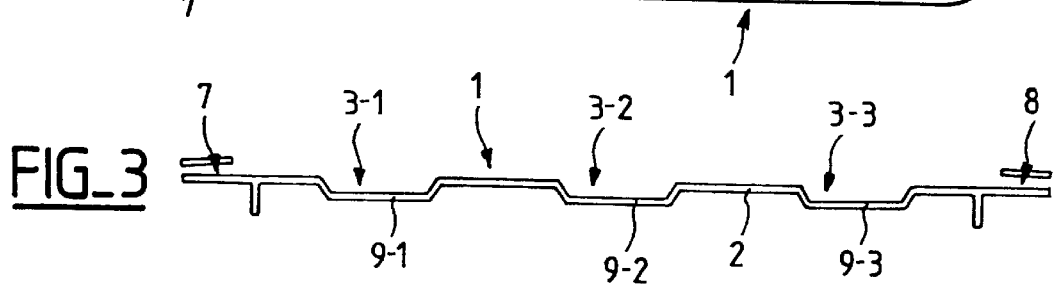
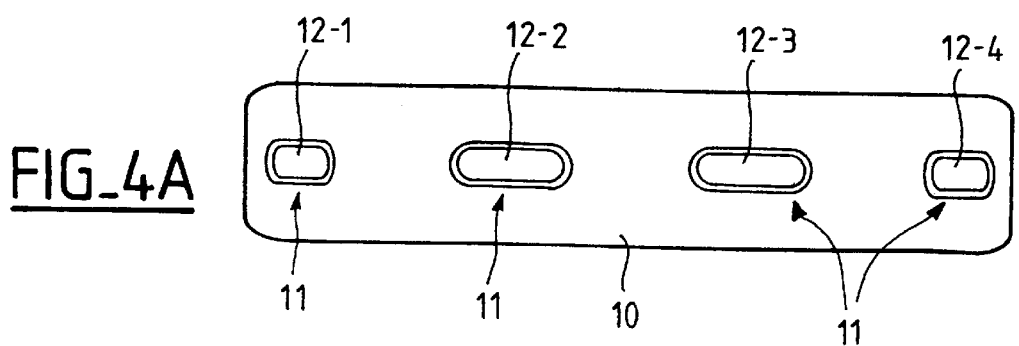
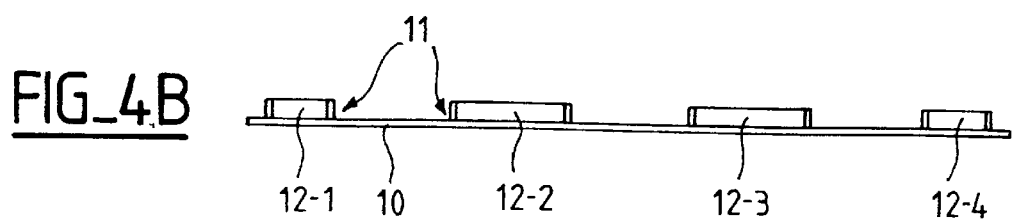

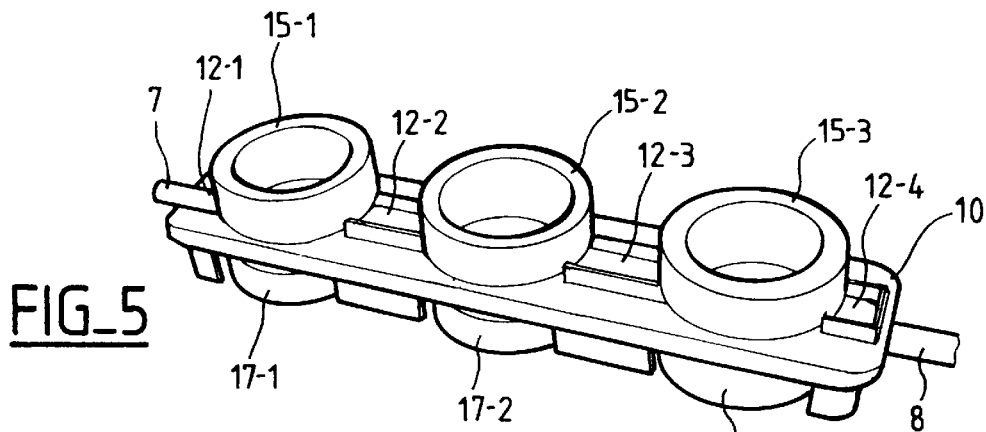
FIG_5
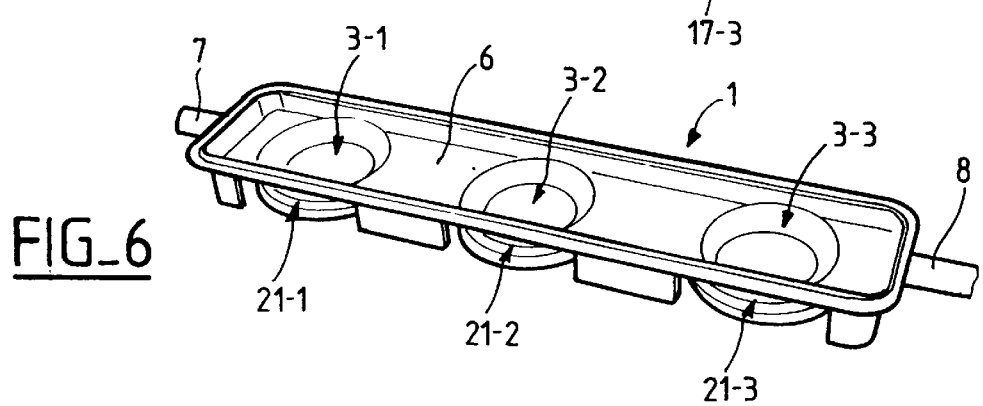
FIG_6
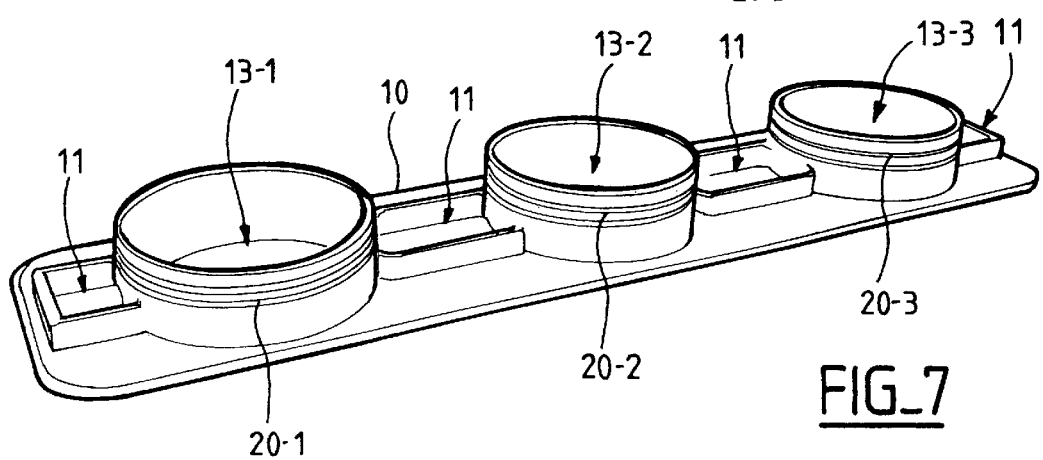
FIG_7
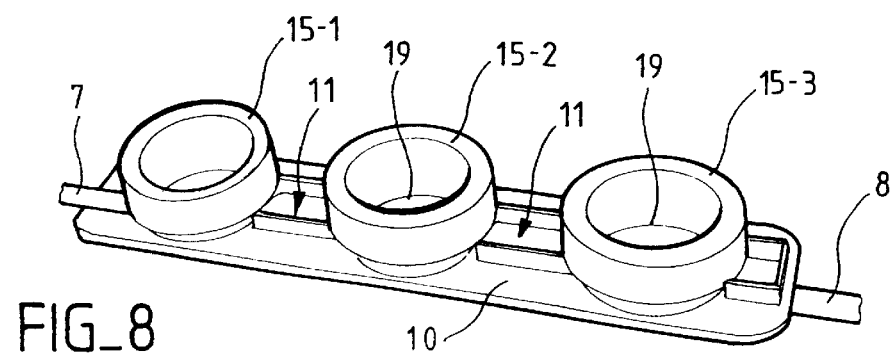
FIG_8

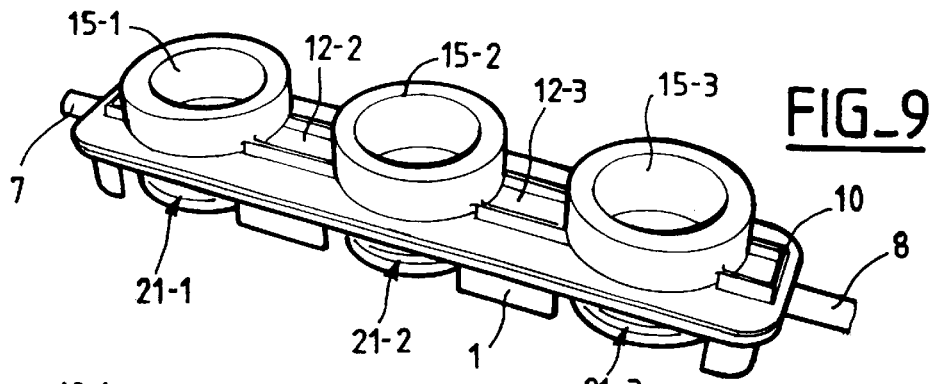
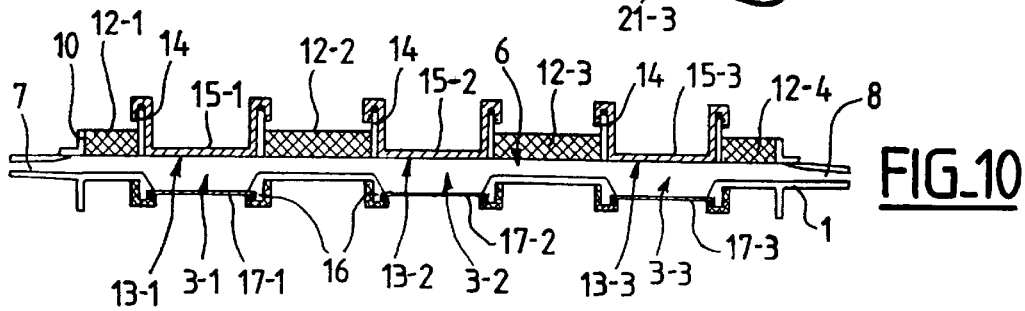
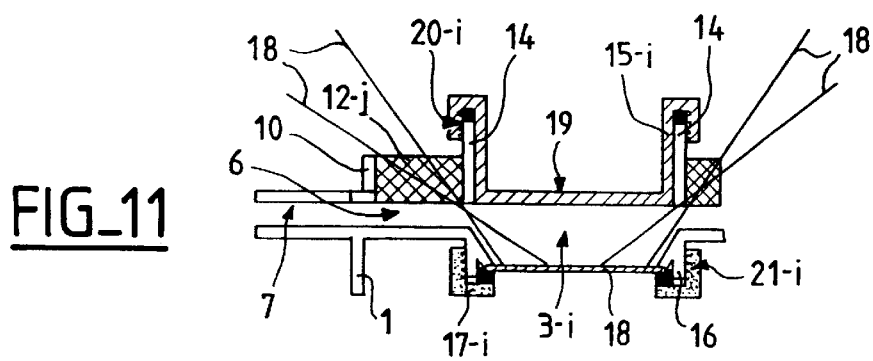
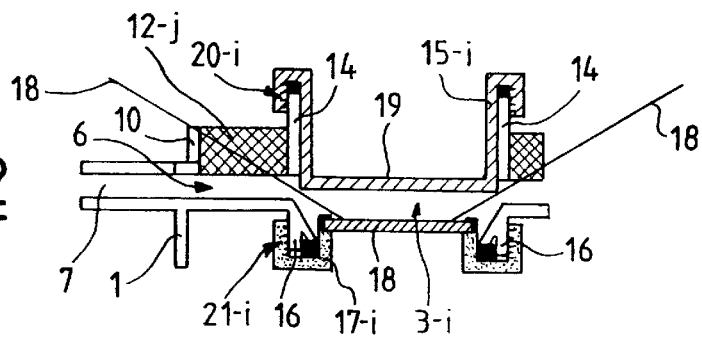
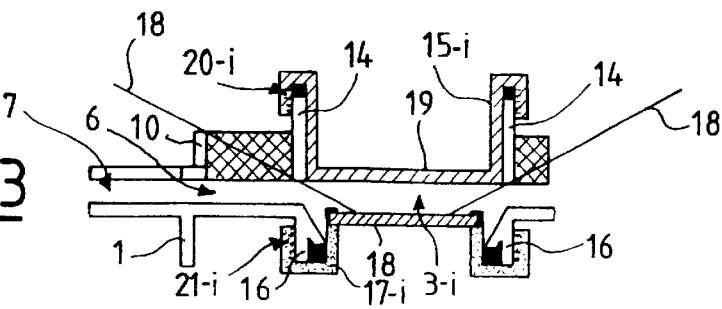

CELL AND TISSUE CULTURE UNIT WITH VARIABLE CONFIGURATION

The invention relates to cell and tissue culture with the help of a culture fluid.

It more particularly relates to cell and tissue culture units which comprise a culture chamber wherein cells and/or tissues to be grown are placed, as well as access means to the chamber capable of being connected to an external device intended for feeding and setting the culture medium (or nutrient) in motion, in order to provide a dynamic culture process in the chamber.

Known culture units are often complex and cumbersome which, because of their integration into the culture device, make difficult the observation of the development of the culture with a microscope. Furthermore, as their complexity makes them very costly, these culture units should be provided for multiple use. It is therefore mandatory that they be disassembled before each new use, in order to clean them, then be re-assembled, which makes their use even more complex and causes changes in results, in the case of successive identical cultures. Consequently, this is detrimental to reproducibility. Moreover, by virtue of their conception, these units do not allow operations to be performed on the cells and tissues during the culture period. On the other hand, as is impossible to change the geometry of the chambers, a specific application generally corresponds to each unit type.

The object of the invention is to overcome all or a part of these drawbacks.

For this purpose, it provides a unit of the type described in the introduction and which comprises a base delimiting at least the side-walls of the chamber and at least the side-walls of at least a well communicating through at least one of its upper and lower portions with the chamber, and removable closing means able to allow access to the chamber and to the well.

Because of their great simplicity and their great adaptability, the units according to the invention may be provided for throw-away uses. Of course, they may also be re-used.

Preferably, the base delimits at least two wells which communicate with the chamber.

In a preferred embodiment, the closing means include a removable upper lid which closes the upper portion of the chamber. Removing the upper lid is then sufficient for accessing the chamber and the well(s). Still more preferably, the upper lid includes, facing the upper portion of each well, a port adapted for receiving a removable upper sealing means, such as a plug. This allows one to operate on a well without having to remove the upper lid.

Upper sealing means having sealing walls placed at different levels may be used in order to force the culture fluid to penetrate the wells.

Advantageously, the upper lid includes at least an area equipped with a means (of the septum type) allowing an external component to be introduced therein, such as a temperature sensor, a pH sensor or a needle.

Moreover, when the lower portion of the wells is not closed by a portion of the base, a lower removable lid which closes all the wells simultaneously, or removable lower sealing means, such as plugs independent of one another, are provided.

The upper lid or at least certain of the lower plugs may be configured so as to receive a culture support.

Lower plugs having sealing walls placed at different levels may be used so as to be able to vary the height of the facing well.

The unit according to the invention may include other features taken separately or combined, and notably:

At least certain of the wells may include at least a membrane in order to define at least two superimposed culture compartments;

at least certain of the side-walls of the well may delimit a cylinder or a truncated cone;

access means may be provided as Luers and equipped with access control means such as valves;

at least one of the septa may be configured so as to deflect the culture fluid flux, preferably towards the wells, or else equipped with an auxiliary component intended for providing this flux deflection;

the base may be made through molding or machining of a synthetic material, preferably resistant to high temperatures which prevail in ovens, in particular in autoclaves, or else resistant to gamma or beta rays, or to any other type of radiation used for sterilization;

it is at least partially made of transparent materials;

it may comprise temperature regulation means.

Other features and advantages of the invention will become apparent on examining the detailed specification hereafter, and the appended drawings, wherein:

FIG. 1 is a perspective view of a base of a unit according to the invention, in a first embodiment, FIG. 2 is a top view of an alternative to the base illustrated in FIG. 1, FIG. 3 is a sectional view of the base illustrated in FIG. 2, FIGS. 4A and 4B are top and sectional views of a first embodiment of the upper lid for cooperating with the bases illustrated in FIGS. 1 and 2, FIG. 5 is a perspective view of a unit according to the invention, in a second embodiment, FIG. 6 is a perspective view of the base of the unit illustrated in FIG. 5, FIG. 7 is a perspective view of the upper lid of the unit illustrated in FIG. 5, FIG. 8 is a perspective view of an alternative upper lid, FIG. 9 is a perspective view of the unit illustrated in FIG. 5, before positioning the lower plugs, FIG. 10 is a sectional view of the unit illustrated in FIG. 5, FIG. 11 details a portion of the unit illustrated in FIG. 10, and FIGS. 12 and 13 are two alternatives to the portion illustrated in FIG. 11.

The appended drawings have essentially a definite character. Accordingly, they may not only serve to complete the invention, but also to contribute to its definition if need be.

In the specification which follows, reference will be made to a culture unit intended for being supplied with a culture fluid (or medium) by any device providing a continuous or intermittent flow by hand or through programming;

Reference is initially made to FIGS. 1–3 in order to describe a first embodiment of a culture unit according to the invention.

In this first embodiment, the culture unit includes a basic block 1 including a lower portion 2 wherein one or several wells 3-i (i=1 to 3 here) are provided, and extended by an upper portion 4 which defines the sidewalls 5 of a chamber 6.

This basic block 1 (or base) is equipped with two access means 7 and 8 intended for supplying the chamber 6 with culture fluid delivered by an external culture device, as indicated above. Both of these access means 7 and 8 may be Luers, for example but they could also be ducts connected to tanks of the external supply device. Further, these access means may be equipped with access control means such as manual or electronic control valves or even valves controlled by compressed air.

Such a basic block may be made of a synthetic material through molding or machining. Preferably, the synthetic material is selected so as to resist to high temperatures of the type that prevail inside decontamination ovens such as autoclaves (generally from 100° to 125° C. over periods of about 30 minutes in a humid environment). However, in other applications, the synthetic material may be selected so as to resist to sterilization by gamma or beta rays or by any other type of radiation, as well as to any other type of sterilization.

In the example illustrated in FIG. 1, the wells 3-i are circular cylindrical holes and the lower portion 2 of base 1 directly defines the bottom 9-i of these wells.

Of course, the wells may assume any type of shape. So, as illustrated in FIGS. 2 and 3, they may also be provided for example, as truncated cones with an apex angle substantially equal to 60°.

In this first embodiment, chamber 6 is closed (insulated from the external wall) by an upper lid 10, of the type illustrated in FIGS. 4A and 4B.

Such a lid is also preferably made of a transparent synthetic material, so as to allow observation of the cells and tissues which are grown inside the chamber 6 and especially in the wells 3-i.

The material used for making the base 1 may also be provided as transparent material in order to allow observation of cultures under several different angles, through a microscope. Further, and in order to facilitate such an observation under a microscope, the unit, and consequently its base and its upper lid 10, has reduced dimensions, as for example a width of about 25 mm and a height of about 10 to 15 mm. But, of course, the units may have different dimensions according to needs and notably according to the types of culture considered.

As illustrated in FIGS. 4A and 4B, the upper lid 10 preferably, includes several areas 11 equipped with means allowing an external component to be introduced such as, notably, a temperature sensor, a pH sensor and a needle for injecting or picking up material from inside the chamber 6 or the wells 3-i.

Preferably, these means adapted for introducing an external component are septa 12-j (j =1 to 4 here). In the example illustrated on FIGS. 4A and 4B, septa 12-j are positioned on the upper lid 10 so as to be located on both sides of the different wells 3-i, as soon as said upper lid 10 is secured with respect to base 1.

At least one or the septa may be configured in order to deflect the culture fluid flux towards at least one of the wells. For this, septa 12-j may protrude into chamber 6, and in this case it has a profile adapted for deflection, or else it is equipped with deflection means such as auxiliary components of the tab type with selected profiles or obstacles of selected shapes.

Reference is made now to FIGS. 5–11 in order to describe a second embodiment of a culture unit according to the invention.

In this second embodiment, as illustrated in FIG. 7, the upper lid 10 includes, between each of its areas 11 equipped with septa 12-j, a port 13-i (i=1 to 3 here) surrounded with substantially vertical walls 14 able to receive a sealing means such as a plug 15-i (i=1 to 3).

Preferably, the vertical walls 14 and the rims of plugs 15-i are equipped with securing means enabling the plugs 15-i to be fixed relatively to he lid 10, sealably. Preferably, this may be a thread 20-i enabling upper plugs 15-i to be screwed on the ends of the vertical walls 14 (see FIG. 8). But of course, any other type of securing means may be considered, such as for example, shape cooperative means or clip means, or elastic clamps or quarter-turn or half-turn locking means. Securement may also result from the relevant shapes of the plugs and the ports of the upper lid, intended for their engagement. For example, the plug may have a conical shape and cooperate with a truncated port.

These plugs, as illustrated in FIGS. 9 to 11, are for being positioned facing the wells 3-i formed in base 1. Consequently, they are preferably made out of a transparent synthetic material.

As better illustrated in FIG. 6, in this second embodiment, the basic block 1 does not include walls 9-i which, as in the first embodiment illustrated in FIGS. 1–4, define the bottom of the wells 3-i. In other words, in this second embodiment, the lower portion of wells 3-i is open.

In this example, access means 7 and 8 are supported by the base 1 and configured so as to feed the chamber 6 via ports formed in the side-wall of said base. In an alternative embodiment illustrated in FIG. 8, access means 7 and 8 are supported by the upper lid 10 and configured for feeding the chamber 6 via ports formed in the side-wall of said lid.

In the example illustrated in FIGS. 9 to 11, each lower part of a well is equipped with substantially vertical walls 16 for receiving lower sealing means, such as a lower plug 17-i. Like for the upper plugs 15-i, securing means, such as for example threads 21-i allowing plugs 17-i to be secured to base 1 through screwing, are provided both on the vertical walls 16 and on the rims of plugs 17-i. Of course, like for the upper plugs, any other type of securing means may be considered.

In such a way, the lower plug's 17-i sealing wall defines the bottom (9-i) of well 3-i.

Of course, instead of using several lower plugs 17-i for closing the lower portions of wells 3-i, a lower lid equipped with as many sealing means as there are wells formed in base 1, may be used.

As illustrated in FIG. 11, through the septa 12-j, it is possible with the help of a needle 18, to inject into or extract matter from (for example cells or nutrients) the inside of wells 3-i, including the bottom of these wells.

As illustrated in FIGS. 12 and 13, the upper and lower sealing means may be provided in different shapes, so as to vary the well geometry. More precisely, by acting on the position of the sealing wall 18 of the lower plugs 17-i, it is possible to vary the height of well 3-i, so as to move the cells or tissues away from the culture fluid flux flowing in chamber 6 (as illustrated in FIG. 11) or else to bring them nearer to this flux (as illustrated in FIGS. 12 and 13).

Also, by acting on the position of the sealing wall 19 of the upper plugs 15-i, "obstacles" (or deflection means) may be created inside the chamber 6, which forces the culture fluid flux down inside the wells 3-i (as illustrated in FIG. 12). The wall, which defines the bottom 19 of an upper plug, may assume a particular shape in order to provide control over deflection. But, as previously indicated, septa may also be used for deflecting the culture fluid flux.

Cultures of different types may be contemplated in the various wells of a unit according to the invention. Accordingly, a unit may include wells equipped with plugs having different geometries.

Further, the plugs may be configured so as to receive culture supports, such as slides (or slip or lamella). This is particularly advantageous as it enables the culture process to be continued after detaching the plug from the culture unit. Actually, certain types of culture processes require two distinct phases: a first "dynamic" phase performed in the presence of a culture fluid flux, wherein this phase is performed in the culture unit according to the invention, and a second "static" phase performed in an incubator. In this situation, sealing for example the open portion of the lower plug, then placing it in an incubator is sufficient for completing the culture process.

Of course, direct placement of the culture unit in an incubator may also be considered, once this unit has been detached from the culture fluid supply device. All types of incubators may be considered, whether dry or wet, so as to provide regulation of the temperature of the cultures.

As an alternative, the culture unit may be equipped with internal temperature regulation means, such as for example a regulation circuit including a temperature sensor and a heating resistor.

On the other hand, and also this is not illustrated in the figures, the lower plugs 17-i may include, in addition to the sealing wall 18, one or more membranes placed at intermediate levels, so as to subdivide the well into sub-compartments for growing different cells or tissues. In this case, it is particularly advantageous when the membranes are notably porous for the culture fluid.

Of course, variability in the well geometry, and the possibility of using culture supports or grids, or even porous membranes, is not limited to the lower plugs. Use of a lower lid provided with sealing means playing the role of plugs may be considered.

Use of lower plugs, as well as upper plugs, is particularly interesting insofar as it allows operations to be performed on a culture grown in a well without this interfering with cultures growing in neighboring wells. Further, possible contamination which occurs when all the wells are simultaneously in the open air, may be reduced.

Finally, any type of device for controlling fluid flow (or culture medium) inside the culture unit according to the invention, may be used. As an example, devices providing a continuous flow, or an alternate flow or peristaltic pumps or syringe injection devices regardless of whether they are manually or electronically controlled (i.e. programmed).

The invention applies to a great number of types of cells and tissues, such as notably:

intestinal cells: Intestine 407, Caco-2, Colo 205, T84, SW1116, WiDr, HT 29, HT 115, HT 55;
epidermal cells: NHEK-Neopooled (Human Epider-mal Keratinocyte Neonatal), Equine Dermis;
cancer cells: HeLa, CHO-K1;
fibroplastic cells of the intestinal type:
CCD18Co
fibroplastic cells of type MRC-5, 3T 3, Wi-38;
myeloma: SP20-Ag14, P3X63 Ag8 653, MPC11;
hybridoma;
normal endothelial human cells:
NHUVEC ("Normal Human Umbilical Vein Endothelial Cells"),
    NHUAEC ("Normal Human Umbilical Artery Endothelial Cells"),
    NHDMC ("Normal Human Dermal Microvascular Cells"),
normal human melanocyte cells: NHEM ("Normal Human Epidermal Melanocytes");
normal human smooth muscle cells:
    HUASMC ("Human Umbilical Artery Smooth Muscle Cells"),
    HPASMC ("Human Pulmonary Artery Smooth Muscle Cells"),
    HAOSMC ("Human Aorta Smooth Muscle Cells");
normal human osteoblast cells: NHOB ("Normal Human Osteoblasts")
insect cells: SF9.

This list is by no means exhaustive; these are only examples.

The invention is not limited to the embodiments of the unit described above, only given as examples, but it encompasses all alternative embodiments which may be considered by one skilled in the art within the scope of the claims hereafter.

Thus, a unit was described wherein the chamber was placed above the wells and therefore communicated with their upper portion. However, the chamber might have been placed below the wells and therefore would have communicated with their lower portion.

Furthermore, bases delimiting substantially identical wells were described, but bases may be considered in which the wells have different shapes so as to achieve possibly different cultures and/or to receive plugs of different shapes.

On the other hand, one of the wells delimited by the base may be subdivided into several sub-wells.

Furthermore, the bottom of the well may be provided with graduations, or more generally markings or patterns, in order to facilitate observation of the development of the culture.

Finally, the culture support may be of the threedimensional type, porous, or gelatinous or even solid, of any shape.

What is claimed is:

1. A cell and tissue culture unit comprising a culture chamber (6) able to receive cells or tissues to be grown, and including access structure (7, 8) to be connected to a culture medium supply device, comprising a base (1) delimiting at least side-walls (5) of the chamber (6) and at least side-walls of at least one well (3-i) communicating through at least one of its upper and lower portions with the chamber (6), and removable closing structure (10, 15-i, 17-i) able to provide access to the chamber (6) and to the well (3-i), said closing structure including a removable upper lid (10) adapted to close the upper portion of said chamber (6), said upper lid (10) including, facing each well (3-i), a port (13-i) adapted to receive a removable upper seal (15-i).

2. A unit according to claim 1, wherein each port (13-i) is configured so as to cooperate with the upper seal (15-i) having sealing walls (19) placed at different levels.

3. A cell and tissue culture unit comprising a culture chamber (6) able to receive cells or tissues to be grown, and including access structure (7, 8) to be connected to a culture medium supply device, comprising a base (1) delimiting at least side-walls (5) of the chamber (6) and at least side-walls of at least one well (3-i) communicating through at least one of its upper and lower portions with the chamber (6), and removable closing structure (10, 15-i, 17-i) able to provide access to the chamber (6) and to the well (3-i), said closing structure including a removable upper lid (10) adapted to close the upper portion of said chamber (6), said upper lid (10) including at least an area (11) configured so as to enable an external component selected from the group consisting of at least one temperature sensor, a pH sensor and a needle (18) to be introduced therein.

4. A unit according to claim 3, wherein said area (11) is equipped with septa.

5. A unit according to claim 4, wherein at least one of the septa (12) is configured in order to deflect the culture fluid flux flowing in the chamber (6).

6. A unit according to claim 4, wherein at least one of the septa (12) is equipped with an auxiliary component adapted to deflect the culture fluid flux flowing in the chamber (6).

7. A cell and tissue culture unit comprising a culture chamber (6) able to receive cells or tissues to be grown, and including access structure (7, 8) to be connected to a culture medium supply device, comprising a base (1) delimiting at least side-walls (5) of the chamber (6) and at least side-walls of at least one well (3-i) communicating through at least one of its upper and lower portions with the chamber (6), and removable closing structure (10, 15-i, 17-i) able to provide access to the chamber (6) and to the well (3-i), said closing structure including a removable lower lid adapted to close the lower portion of each well (3-i).

8. A unit according to claim 7, wherein the lower lid or at least certain of the lower seals (17-i) are configured for receiving a culture support.

9. A cell and tissue culture unit comprising a culture chamber (6) able to receive cells or tissues to be grown, and including access structure (7, 8) to be connected to a culture medium supply device, comprising a base (1) delimiting at least side-walls (5) of the chamber (6) and at least side-walls of at least one well (3-i) communicating through at least one of its upper and lower portions with the chamber (6), and removable closing structure (10, 15-i, 17-i) able to provide access to the chamber (6) and to the well (3-i), said closing structure including removable lower seals (17-i) independent of one another and each configured so as to close the lower open portion of a well (3-i).

10. A unit according to claim 9, wherein each open lower portion of a well (3-i) is configured so as to cooperate with a lower seal (17-i) or a lower lid having sealing walls (18) placed at different levels so as to vary the height of the facing well (3-i).

11. A cell and tissue culture unit comprising a culture chamber (6) able to receive cells or tissues to be grown, and including access structure (7, 8) to be connected to a culture medium supply device, comprising a base (1) delimiting at least side-walls (5) of the chamber (6) and at least side-walls of at least one well (3-i) communicating through at least one of its upper and lower portions with the chamber (6), and removable closing structure (10, 15-i, 17-i) able to provide access to the chamber (6) and to the well (3-i), wherein at least certain of the wells (3-i) include at least one membrane placed at an intermediate level so as to define at least two superimposed culture compartments.

* * * * *